US008523938B2

(12) United States Patent
Takeuchi et al.

(10) Patent No.: US 8,523,938 B2
(45) Date of Patent: Sep. 3, 2013

(54) STENT

(75) Inventors: Ryohei Takeuchi, Kanagawa (JP);
Kazuhiro Maruyama, Kanagawa (JP);
Noboru Saito, Kanagawa (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 103 days.

(21) Appl. No.: 13/044,663

(22) Filed: Mar. 10, 2011

(65) Prior Publication Data

US 2011/0202122 A1    Aug. 18, 2011

Related U.S. Application Data

(63) Continuation of application No. PCT/JP2009/065591, filed on Sep. 7, 2009.

(30) Foreign Application Priority Data

Sep. 17, 2008    (JP) .................................. 2008-238058

(51) Int. Cl.
*A61F 2/06* (2013.01)
*B05D 5/00* (2006.01)

(52) U.S. Cl.
USPC .......... 623/1.46; 623/1.42; 427/256; 427/287

(58) Field of Classification Search
USPC .............................................. 623/1.42, 1.46
See application file for complete search history.

(56) References Cited

U.S. PATENT DOCUMENTS

| | | | |
|---|---|---|---|
| 6,395,326 B1 * | 5/2002 | Castro et al. ................. | 427/2.24 |
| 6,805,898 B1 * | 10/2004 | Wu et al. ..................... | 427/2.25 |
| 6,979,346 B1 * | 12/2005 | Hossainy et al. ............ | 623/1.11 |
| 7,014,654 B2 * | 3/2006 | Welsh et al. ................. | 623/1.15 |
| 7,335,314 B2 * | 2/2008 | Wu et al. ........................ | 216/10 |
| 7,628,807 B2 * | 12/2009 | Flanagan ..................... | 623/1.42 |
| 7,837,726 B2 * | 11/2010 | Von Oepen et al. ......... | 623/1.44 |
| 2005/0015142 A1 * | 1/2005 | Austin et al. ................. | 623/1.42 |

(Continued)

FOREIGN PATENT DOCUMENTS

JP    2007-97706 A    4/2007
WO   WO 2007/083797 A1   7/2007

OTHER PUBLICATIONS

International Search Report (PCT/ISA/210) issued on Nov. 2, 2009, by Japanese Patent Office as the International Searching Authority for International Application No. PCT/JP2009/065591.

*Primary Examiner* — David Isabella
*Assistant Examiner* — Jacqueline Woznicki
(74) *Attorney, Agent, or Firm* — Buchanan Ingersoll & Rooney PC

(57) ABSTRACT

A stent includes a stent body in which struts are joined mutually while intersecting and which is formed tubularly as a whole, and a drug coat layer on the outer surface of the struts. The strut has a bend which is deformed as the stent body expands/contracts in the radial direction, and the drug coat layer with which the bend is coated is formed in such a manner that the drug coat layer is mountain-shaped in a cross-section perpendicular to the axis of the strut and the ridgeline of the mountain shape extends in a wavy shape along the longitudinal direction of the strut. The drug coat layer deforms relatively easily without using plasticizer as the stent deforms and is not so susceptible to causing problems such as peeling, destruction, damage or falling off of the drug coat later.

20 Claims, 9 Drawing Sheets

(56) References Cited

U.S. PATENT DOCUMENTS

| | | | |
|---|---|---|---|
| 2006/0095123 A1* | 5/2006 | Flanagan | 623/1.46 |
| 2008/0033536 A1 | 2/2008 | Wittchow | |
| 2009/0264975 A1* | 10/2009 | Flanagan et al. | 623/1.2 |
| 2009/0276036 A1 | 11/2009 | Nagura et al. | |
| 2010/0114303 A1* | 5/2010 | Su et al. | 623/1.46 |
| 2012/0165923 A1* | 6/2012 | Maruyama et al. | 623/1.42 |

* cited by examiner (A)

(B)

(C)

(D)

(A)

(B)

(C)

(D)

STENT

This application is a continuation of International Application No. PCT/JP2009/065591 filed on Sep. 7, 2009, and claims priority to Japanese Application No. 2008-238058 filed on Sep. 17, 2008, the entire content of both of which is incorporated herein by reference.

TECHNICAL FIELD

The present invention relates to a stent to be put indwelling in a stenosed or occluded lesion generated in a lumen in vivo so as to maintain patency of the lumen.

BACKGROUND DISCUSSION

A stent is a medical device used to ameliorate a stenosed or occluded lesion generated in a lumen in vivo such as a blood vessel, a bile duct, a trachea, an esophagus, an urethra, etc. A stent is a netting-like tubular body in which thin struts are joined mutually while intersecting at joints.

Stents are classified, by their function and the manner in which they are indwelled, into two general classifications, self-expandable stents and balloon-expandable stents. A self-expandable stent is a stent which itself has an expanding function, is stored in a catheter in a preliminarily radially contracted state, and is allowed to expand by releasing the contracted state after the stent is positioned in a target lesion so that the stent is fixed in close contact with a lumen. A balloon-expandable stent is a stent which itself does not have an expanding function, but rather is expanded by a balloon positioned in the stent after the stent is positioned in the target lesion, whereby the stent is plastically deformed and fixed in close contact with a lumen.

For instance, in relation to the coronary artery of a heart, a balloon-expandable stent is generally used for the purpose of preventing restenosis after percutaneous transluminal coronary angioplasty (PTCA). In practicing a therapeutic treatment, the stent is mounted onto the outer periphery of a balloon at the distal end of a catheter in a radially contracted state. After insertion into a living body, the stent is expanded (dilated) by the balloon in a target lesion of a lumen and is fixed in close contact with the inner wall of the lumen. The stent is left indwelling in the coronary artery to maintain a dilated state or patency of the stenosed or occluded lesion.

In the case of a stent indwelled in a lumen, the restenosis rate is lower as compared with the case where only PTCA is performed; however, restenosis in the stent indwelling lesion has been observed at a rate of about 20 to 30%. The principal cause of the restenosis is intimal hypertrophy due to migration/growth of blood vessel smooth muscle cells. Recently, therefore, development has been made of stents of the drug eluting type, called DES (Drug Eluting Stents), in which the outer surface of a stent is coated with a drug capable of suppressing the migration/growth of blood vessel smooth muscle cells, and the drug is eluted in the stent indwelling lesion to thereby prevent restenosis.

Examples of the drug include an antibiotic agent such as sirolimus or a carcinostatic agent or the like. Coating with the drug is carried out by a method in which a coating solution prepared by dissolving the drug and a biocompatible polymer in a solvent is applied to the surface of a stent by a dipping method, a spraying method or a so-called direct coating method (applying the solution to the stent along struts which constitute the stent) or the like so that a predetermined quantity of the drug is present on the stent surface, followed by drying to effect solidification.

To put (indwell) a DES in a lumen, however, the stent is radially contracted, is then delivered into the lumen in the contracted state, and is thereafter expanded for indwelling. A problem can thus arise in that the drug coat layer is peeled from the stent surface or tends to be destructed upon expanding/contracting deformation of the stent. In the stents of either type, it is preferable that the stent has flexibility allowing the stent to be deformable not only in the radial direction but also in the axial direction, for coping with a larger number of cases. From this point of view, it is preferable that peeling of the drug coat layer is inhibited or prevented from occurring upon deformation in any direction.

Japanese Patent Laid-Open No. 2007-97706 (for example claim 1 and paragraph No. [0020]) discloses a stent in which a drug coat layer is formed by use of a composition containing a plasticizer. When a plasticizer is thus contained in the drug coat layer, the drug coat layer itself has flexibility and, therefore it is deformed according to expanding/contracting deformations of the stent. This is preferable for preventing the situations of peeling, destruction, damage or falling off of the drug coat layer.

However, a plasticizer is, so to speak, an oil component. Where this substance is put into a lumen in vivo, therefore, it may clog up a peripheral blood vessel if not biodegraded. Even if the plasticizer is biodegraded, it may produce a bad influence on the living body, depending on the type of plasticizer.

SUMMARY

The stent disclosed here includes a drug coat layer which is able to deform relatively easily, preferably without using plasticizer, in association with deformation of the stent and which is not as susceptible to peeling, destruction, damage or falling off of the coat layer as in other known stents.

The stent disclosed here includes a tubular stent body in which struts are joined mutually while intersecting, with a drug coat layer coating outer surfaces of the struts. The struts have bends which deform as the stent body expands or contracts in the radial direction, and the drug coat layer coated on the bend is formed in such a manner that its shape in cross-section perpendicular to the axis of the strut is mountain shape and the ridgeline of the mountain shape extends in a wavy shape along the longitudinal direction or longitudinal extent of the strut.

The configuration of the drug coat layer coating the bend of the strut helps ensure that even when the stent body is deformed in the radial direction and/or the axial direction, and the bend undergoes expanding or contracting deformation, the drug coat layer is also able to deform in a manner following this deformation of the bend. Therefore, peeling of the drug coat layer from the strut or destruction, damage or falling off of the drug coat layer itself is inhibited and not as likely to occur, and a predetermined quantity of the drug can be released from the stent to a target lesion in a sustained and desired manner.

The drug coat layer can be physically deformed without using a plasticizer and so the stent does not exhibit bad influence on the living body typically accompanying the use of a plasticizer and is relatively high in safety.

Moreover, the drug coat layer in a dried and solidified state is not significantly at risk of falling off, even upon application of an external force, for example upon contact with the inner wall of a lumen in vivo. Thus, a predetermined quantity of the drug can be maintained, the stent is relatively easy to handle, the procedure for using the stent is quite easy and assured, and the stent is extremely convenient to use.

The bend may be a gradually circular-arched shape bend. This helps ensure that relatively little strain is exerted on the drug coat layer when the bend is opened wider. There is thus obtained a relatively high restraining effect on the occurrence of peeling, destruction, damage or falling off of the drug coat layer.

The drug coat layer may be so configured that a peak of the wavy ridgeline shape of the drug coat layer is located in the vicinity of an outer-side inflection point of the bend (which is, for example, U-shaped) of the strut when the struts are opened wider in association with expanding/contracting deformation of the stent body. This helps ensure that the drug coat layer possesses a relatively large material thickness at a part where little strain is exerted when the bend is opened wider. Accordingly, a large quantity of a drug can be applied or coated on the stent, while restraining such a problem as peeling of the drug coat layer.

The drug coat layer may be absent in the vicinity of an inner-side inflection point of the bend (which is, for example, U-shaped) of the strut when the struts are opened wider in association with expanding/contracting deformation of the stent body. This helps ensure that the drug is absent at that portion of the bend at which the bend is most expanded (extended). Consequently, the occurrence of peeling of the drug coat layer is further restrained.

The bend may be provided with the drug coat layer in such a manner that an odd number of peaks of the wavy ridgeline shape are present there. When the bent portion is deformed, the drug coat layer is relatively easily deformed with the peaks of the wavy shape as centers of deformation, and the drug coat layer deforms in a manner following the deformation of the strut. The occurrence of peeling of the drug coat layer is thus further restrained.

The drug coat layer may be formed not only on the bend but also on the whole or a part of the outer surface of the strut in such a manner that a ridgeline of the drug coat layer extends in a wavy shape along the longitudinal direction or longitudinal extent of the strut. This helps ensure that even in the case where not only the bend tending to be opened wider but also other parts of the stent, for example a rectilinear part, is also deformed, the strain exerted on the drug coat layer due to this deformation can be dispersed. Consequently, the restraining effect on potential peeling of the drug coat layer is improved.

The drug coat layer may be formed using a mixture of a drug and a polymer. This helps facilitate coating the outer surface of the struts, and enhances workability.

Examples of the polymer include a biodegradable polymer, for example, polylactic acid, polyglycolic acid, or a lactic acid-glycolic acid copolymer. This helps ensure that after the stent is put indwelling in a living body, the polymer covering and protecting the drug is biodegraded, whereby the drug is released in a sustained manner, and restenosis at the stent indwelling lesion is inhibited or prevented.

According to another aspect, a stent comprises a longitudinally extending stent body that includes a plurality of axially arranged annular members in which axially adjacent annular members are connected to one another, with each annular member comprising a plurality of longitudinally extending parts each possessing a width-wise extent and a lengthwise-extent, and with the plurality of longitudinally extending parts being connected to one another by curved parts each possessing a width-wise extent and a lengthwise-extent. The stent body is radially outwardly expandable from a contracted state to an expanded state, and the curved parts are deformed during the radial outward expansion of the stent body. A drug coat layer is located on the outer surface of a plurality of the curved parts of each of the plurality of annular members. The drug coat layer on each of the plurality of curved parts varies in thickness in the width-wise extent of the respective curved part, with the drug coat layer on each of the plurality of curved parts possessing a ridgeline extending along a lengthwise extent of the respective curved part, the ridgeline being the portion of the drug coat layer having the greatest thickness. The ridgeline of the drug coat layer on each curved part crossing the longitudinal centerline of the curved part at a plurality of spaced apart locations so that for each curved part, the ridgeline is positioned entirely on one side of the longitudinal centerline over one longitudinal portion of the curved part and is positioned entirely on the opposite side of the longitudinal centerline over a different longitudinal portion of the curved part.

An additional aspect of the disclosure here involves a stent comprising a longitudinally extending stent body in which a plurality of annular members are arranged axially and so that axially adjacent annular members connected to one another, wherein each annular member includes a plurality of interconnected struts each having a longitudinal centerline along a longitudinal extent of the strut, and wherein each strut also has a width-wise extent and a lengthwise-extent, and the struts include curved parts and longitudinally extending parts. The stent body is radially outwardly expandable from a contracted state to an expanded state to cause at least some of the struts to deform. A drug coat layer is located on the outer surface of a plurality of the struts of each of the plurality of annular members. The drug coat layer on each strut varies in thickness in the width-wise extent of the respective strut, and the width-wise location of the greatest thickness of the drug coat layer on each strut varies along the lengthwise extent of the strut. The drug coat layer has a ridgeline which follows the portion of the drug coat layer having the greatest thickness, and the ridgeline of the drug coat layer in each strut being wavy-shaped in plan view.

Further aspects, features and characteristics of the stent here will be apparent by taking into account the preferred embodiments shown as an example in the following description and the accompanying drawings.

BRIEF DESCRIPTION OF THE DRAWING FIGURES

Figure 4:
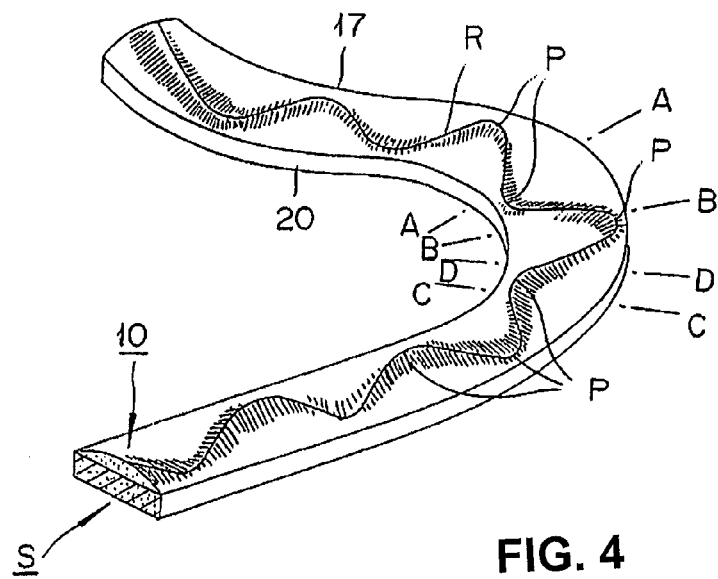
FIG. 4 is a perspective view of a bend in the stent shown in FIG. 1.
Figure 5:
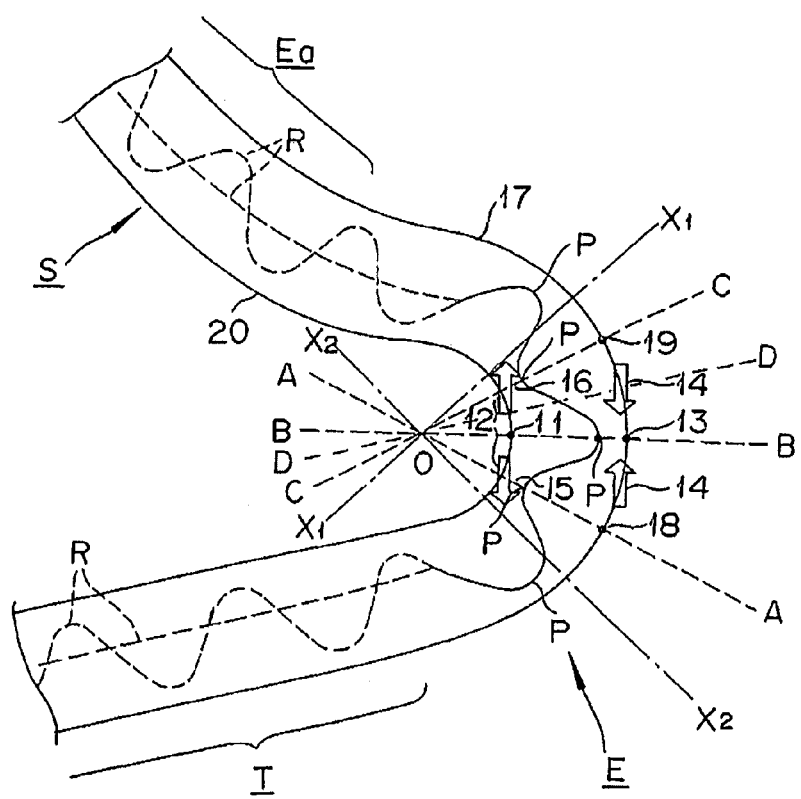
FIG. 5 is a view showing a deformed state of the bend when the bend is opened wider.

FIGS. 6(A)-6(D) are cross-sectional views of a drug coating layer on the stent, taken along the section lines A-A, B-B, C-C, and D-D in FIGS. 4 and 5.

FIGS. 7(A)-7(D) are cross-sectional views showing a modification of the drug coat layer on the stent.

FIGS. 8(A)-8(D) are cross-sectional views showing another modification of the drug coat layer on the stent.

Figure 9:
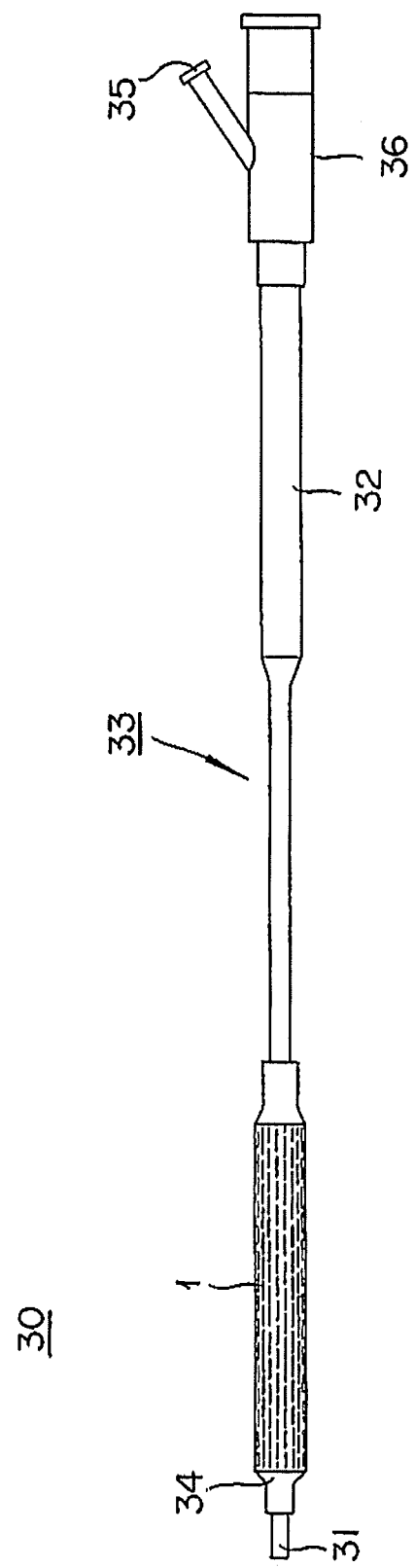

FIG. 9 is a front view of a living organ dilating device.

Figure 10:
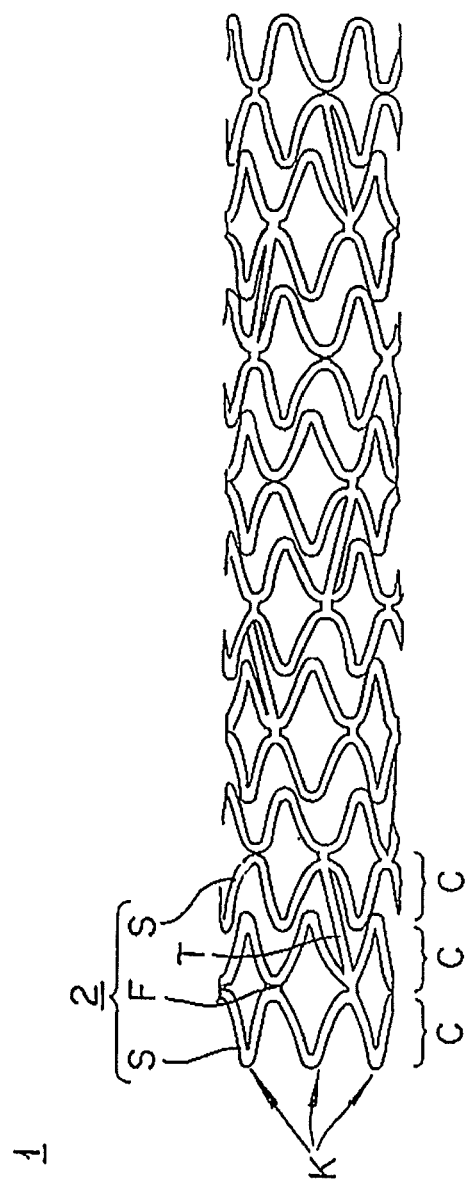

FIG. 10 is a front view of a major part of a stent according to another embodiment disclosed here.

DETAILED DESCRIPTION

A stent according to an embodiment disclosed here is a so-called balloon-expandable type stent. The stent is a tubular body having a netting construction in which, generally, a plurality of thin struts S are mutually joined and intersect at intersecting joints F. The stent has an outer diameter, in the collapsed state, sized to permit insertion of the stent into a living body, and is expandable in the radial direction and/or the axial direction when a radially outwardly directed force for radially outwardly expanding the stent is exerted or applied from the inside the tubular body.

More specifically, the stent 1 has: a stent body 2 in which struts S with a predetermined width and having various shapes, for example curved parts or bends K formed by bending or curving, and straight parts or straights T, extend continuously, with ends of some of the struts S being joined mutually by joints F, and with openings O or spaces formed between the struts S so that the bends K and the straight parts T are deformable; and a drug coat layer 10 (see FIG. 4) formed by coating outer surfaces of the struts S with a drug.

Figure 1:
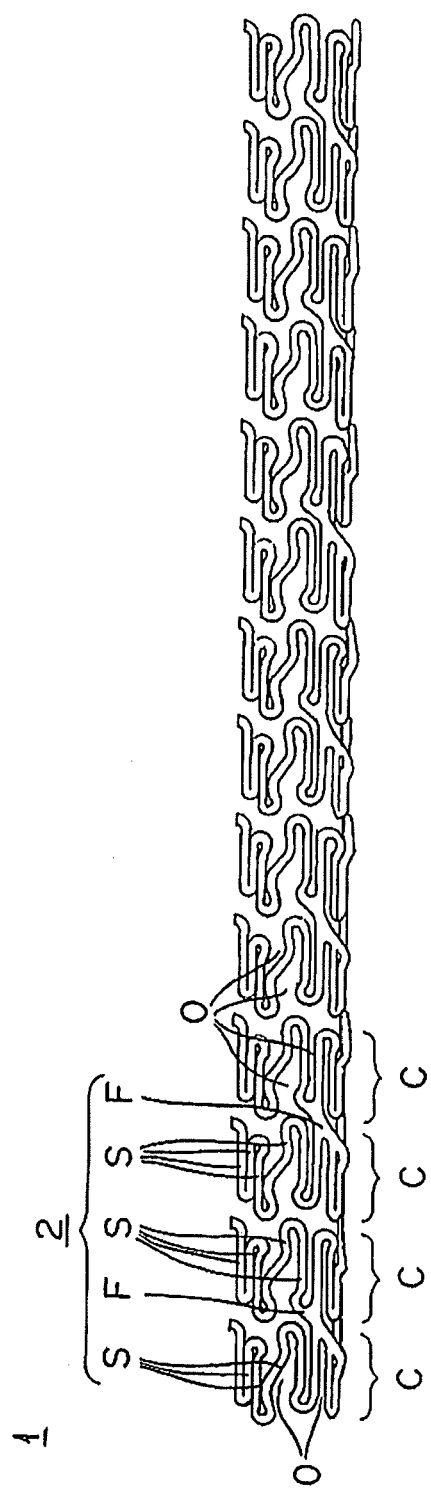
FIG. 1 is a front view of a stent according to an embodiment disclosed here.
Figure 2:
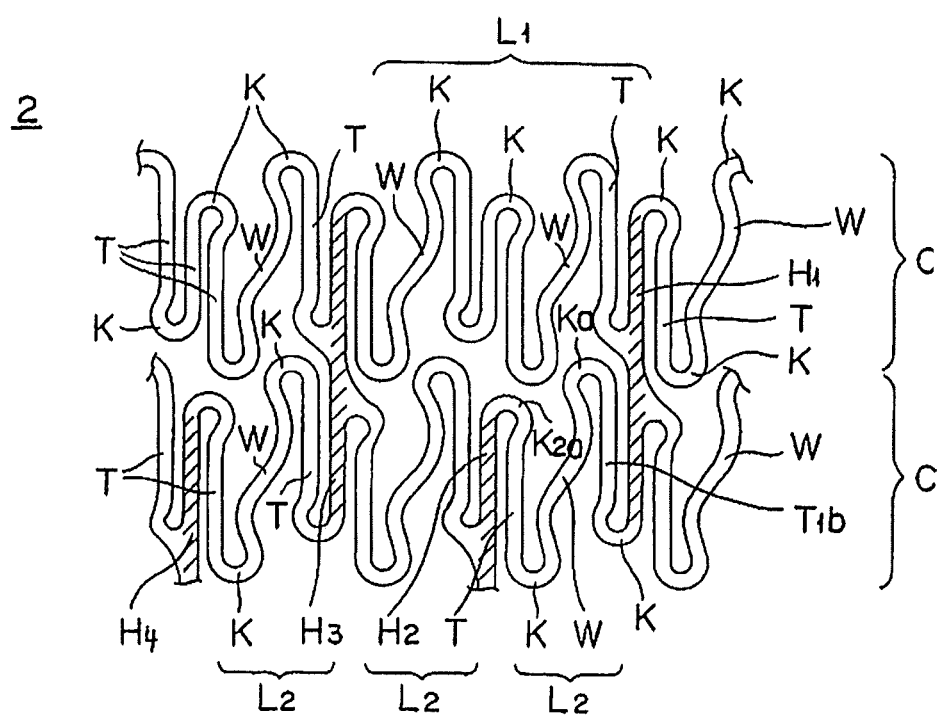
FIG. 2 is an enlarged plan view showing a condition where a cell portion of the stent shown in FIG. 1 is developed.

The strut S, as shown in FIG. 2, has parallel parts H1-H4 (shaded for clear presentation) extending parallel to the center axis of the stent 1 (and parallel to each other). The bends K curve gradually in a semi-circular arched shape, and the straight parts T are continuous with (extend directly from) the bends K. The parallel parts H1-H4, the bends K, the straight parts T and wavy parts W combine to form annular members C having a predetermined pattern. The stent body 2 has a predetermined length in the axial direction by virtue of a plurality of the annular members C being arranged in axial succession while joining axially adjacent ones of the annular members at the joints F, which are central portions of the parallel parts H. For example, the stent body 2 shown in FIG. 1 includes fourteen axially arranged annular members C, though the number of annular members C can vary and can be appropriately selected as desired and required.

Beginning at the left of the upper annular member C shown in FIG. 2, the upper annular member C includes the following arrangement—a straight part T, a lower bend K, a straight part T, an upper bend K, a straight part T, a lower bend K, a wavy part W, an upper bend K, a straight part T, a central bend K of the parallel part H3, the upper half of the parallel part H3, an upper bend K, a straight part T, a lower bend K, a wavy part W, an upper bend K, a straight part T, a lower bend K, a straight part T, an upper bend K, a straight part T, a lower bend K, a wavy part W, an upper bend K, a straight part T, a central bend of the parallel part H1, the upper half of the parallel part H1, an upper bend K, a straight part T, a lower bend K, and a wavy part W.

Beginning at the left of the lower annular member C shown in FIG. 2, the lower annular member C includes the following arrangement—a straight part T, a central bend of the parallel part H4, the upper half of the parallel part H4, an upper bend K, a straight part T, a lower bend K, a wavy part W, an upper bend K, a straight part T, a lower bend K of the parallel part H3, the lower half of the parallel part H3, a central bend of the parallel part H3, a straight part T, a lower bend K, a wavy part W, an upper bend K, a straight part T, a central bend of the parallel part H2, the upper half of the parallel part H2, an upper bend K, a straight part T, a lower bend K, a wavy part W, an upper bend K, a straight part T, a central bend K of the parallel part H1, a lower part of the parallel part H1, a central bend of the parallel part H1, a straight part T, a lower bend K, and a wavy part W.

To be more specific, as shown in FIG. 2, the stent body 2 is constructed to include the parallel parts H1, H2, H3 and H4 (each being part shaded in the figure) which are arranged in a staggered manner, each parallel part H being provided at its central portion with the bends K which project in opposite directions. The (upper) central bend K of the parallel part H1 and the upper end of the parallel part H3 are interconnected by a relatively longer zigzag connection line L1 in which a plurality of the straight parts T and slanted (diagonally oriented) wavy parts W are connected through the bends K. On the other hand, the lower end of the parallel part H1 and the upper end of the parallel part H2 are interconnected by a relatively shorter zigzag connection line L2 in which two straight parts T and one wavy part W are connected through a plurality of bends K.

The lower-end bend K of the parallel part H1 and the upper end of the parallel part H2 are interconnected through a relatively shorter zigzag connection line L2. Similarly, the central bend K of the parallel part H2 and the central bend K of the parallel part H3 are interconnected through a relatively shorter zigzag connection line L2, and the lower-end bend K of the parallel part H3 and the upper-end bend K of the parallel part H4 are interconnected through a relatively shorter zigzag connection line L2. The central bend K of the parallel part H3 and the upper end of the parallel part H1 are interconnected through the relatively longer zigzag connection line L1.

Preferably, the straight part T is parallel (inclusive of substantially parallel) to the center axis of the stent 1 before the stent 1 is expanded, namely when the stent 1 is compressed. The lower bend K of the wavy part W in the upper annular member enters into the space between the central bend of the parallel part H1, H3 and the upper bend K of the wavy part W (or the space between the upper bends K of the wavy parts W) in the axially adjacent lower annular member. This configuration helps ensure that the outside diameter upon compression of the stent 1 is relatively small, the stent can be opened wider upon expansion, and the so-called expansion holding force is relatively large.

With respect to the bends K, acute-angle bending is not preferable. Instead, U-shaped or gradual circular-arched bending or curving is preferred. This helps ensure that relatively little strain is exerted on the drug coat layer when the bend K is opened wider, and the restraining effect on problems such as peeling, destruction, damage or falling off of the drug coat layer is quite high. It is to be noted here, however, that the bend K may be in a curved shape which does not largely bulge to the outer side. This helps ensure that the outside diameter upon compression of the stent 1 is relatively small, which is advantageous for insertion into a living organ (e.g., blood vessel) having a relatively small diameter.

The material for forming the stent 1 is preferably a material with a certain degree of biocompatibility, for example stainless steels, tantalum or tantalum alloys, platinum or platinum alloys, gold or gold alloys, cobalt-based alloys, cobalt-chromium alloys, titanium alloys, niobium alloys, or the like. Among stainless steels, SUS316L is preferred as it is the most corrosion-resistant.

After the stent is formed into a predetermined pattern, the stent 1 may be plated with a noble metal (gold, platinum). The stent 1 may also be annealed after being formed into the intended shape. By annealing, it is possible to enhance flexibility and plasticity of the stent as a whole, to improve indwelling performance of the stent in a bent blood vessel, to reduce physical stimuli given to the blood vessel inner wall, and to lessen the causes of restenosis. To avoid formation of an oxide film on the stent surface, the annealing is preferably carried out by heating to a temperature of 900 to 1200° C. in an inert gas atmosphere (e.g., in a nitrogen-hydrogen mixed gas), followed by slow cooling.

The stent 1 is preferably so configured that the area occupied by the struts S in the condition where the stent 1 is mounted on a balloon 34 (described later) is 60 to 80% based on the whole area of the outer peripheral surface of the stent 1 inclusive of the openings O.

The width of the struts S is preferably about 90 to 100 μm. The length of each cell portion C in the axial direction is preferably 0.5 to 2.0 mm, particularly preferably 0.9 to 1.5 mm. The length of the parallel part H in the axial direction is preferably about 1.0 to 4.0 mm, particularly preferably 1.5 to 3.0 mm.

The diameter of the stent 1 when not expanded is preferably about 0.8 to 2.5 mm, more preferably 0.9 to 2.0 mm. The length of the stent 1 when not expanded is preferably about 8 to 40 mm.

The fabrication of the stent 1 is carried out by removing portions from a tubular body, specifically a metallic pipe, other than the struts. For instance, the openings O shown in FIG. 1 are removed from a metallic pipe by an etching method in which masking and a chemical agent are used and which is called photo-fabrication, an electric discharge machining using a die, a cutting method (e.g., mechanical polishing, laser cutting) or the like.

After the fabrication is carried out as described above, edges of the struts S are removed by chemical polishing or electropolishing, to finish the stent surfaces to smooth surfaces. Further, the inner surface and/or the outer surface of the struts S may be coated with a biocompatible material. The biocompatible material is preferably a biocompatible synthetic resin or metal. Examples of the method for coating the surface(s) of the stent 1 with an inert metal include gold plating by use of electroplating, stainless steel plating by use of vapor deposition, silicon carbide or diamond-like carbon or titanium nitride plating or gold plating by use of sputtering. The synthetic resin can be selected from among thermoplastic or thermosetting resins. Examples of the synthetic resin include polyolefins (e.g., polyethylene, polypropylene, ethylene-propylene copolymer, etc.), polyvinyl chloride, ethylene-vinyl acetate copolymer, polyamide elastomers, polyurethane, polyesters, fluoro-resins, silicone resins, parylene, etc., among which preferred are polyolefins, polyamide elastomers, polyesters, polyurethane, silicone resins, and parylene. Biodegradable resins (e.g., polylactic acid, polyglycolic acid, lactic acid-glycolic acid copolymer) may also be used. The synthetic resin film is preferably flexible to such an extent as not to hinder curving of the struts S, and the material thickness of the film is 3 to 300 μm, preferably 5 to 100 μm.

In this embodiment, the stent 1 formed as above is subjected to formation of the drug coat layer 10 on the outer surfaces of the struts S, as shown in FIG. 4.

The drug coat layer 10 is formed on the struts S, specifically on the parts which intrinsically have an extremely small width of 90 to 100 μm. In view of this, the drug coat layer 10 is preferably formed by a method in which the stent body 2 is coated with a coating solution along the struts S over the whole width thereof at a time, thereafter the coating solution is dried and solidified, and the solvent is evaporated off, leaving a predetermined quantity of the drug on the outer surface of the stent body 2.

The drug coat layer 10 thus formed is united to the struts S. In addition, the layer itself is less liable to be extended or flexed and is brittle. Therefore, when the metallic stent body 2 undergoes expanding/contracting deformation, the drug coat layer 10 cannot follow this deformation, and so peeling or falling off of the drug coat layer 10 from the strut S, or cracking, destruction or damaging of the drug coat layer 10 can occur.

Figure 3:
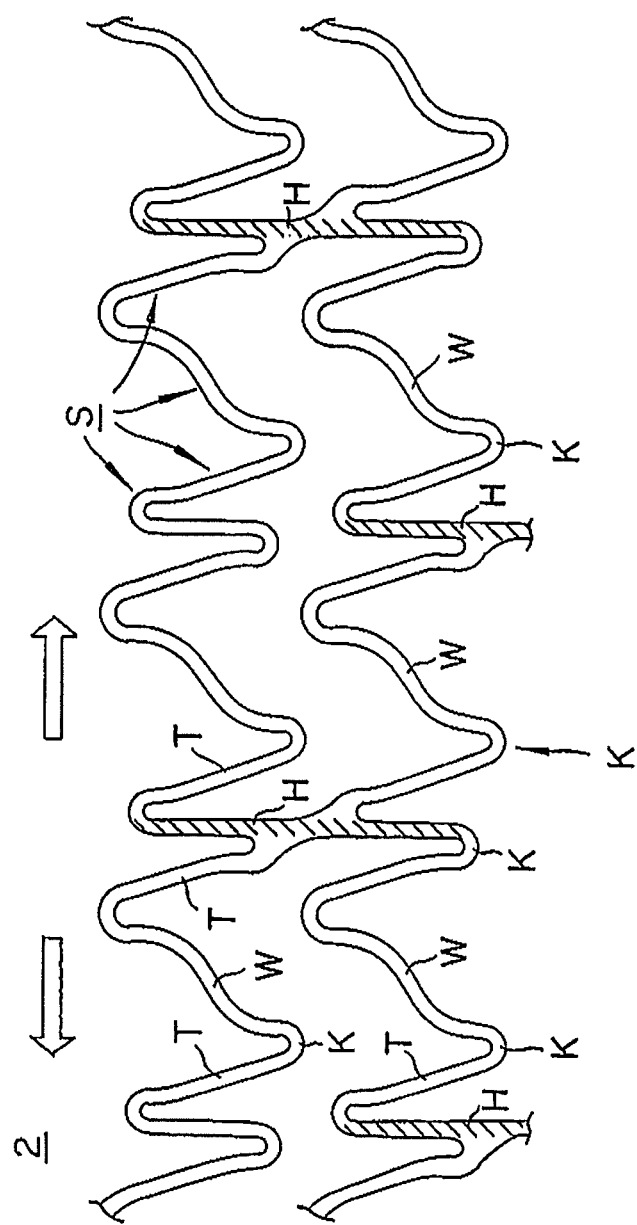
FIG. 3 is a developed enlarged plan view showing a condition where the cell portion is expanded from the condition shown in FIG. 2.

This point is further discussed as follows. For instance, when the stent body 2 is deformed to expand outward in the radial direction, the bend K is opened wider in the directions of arrows as shown in FIG. 3. In the case of the bend K which is U-shaped, the spacing between both struts S is opened wider. In this case, as shown in FIG. 5, of the U-shaped bend K, the portion in the vicinity of an inner-side inflection point 11 of the strut S (a point which corresponds to a pole when the U-shaped bend K is grasped as a quadratic function and which is the inner-side pole of the strut S having a predetermined width) undergoes an expanding (extending) action as indicated by the void arrows 12, whereas the portion in the vicinity of an outer-side inflection point 13 (a point which corresponds to a pole when the U-shaped bend K is grasped as a quadratic function and which is the outer-side pole of the strut S having a predetermined width) undergoes a contracting action as indicated by the void arrows 14.

Of the drug coat layer 10 on which forces in the above-mentioned relationship are exerted, the portion in the vicinity of the inner-side inflection point 11 cannot follow the extending deformation of the strut S and so this portion is cracked through tearing-up. On the other hand, the portion in the vicinity of the outer-side inflection point 13 cannot follow the contracting deformation of the strut S, so that this portion undergoes peeling or collapse.

The greatest reason for this phenomenon is that the drug coat layer 10 is formed substantially uniformly over the whole width of the strut S.

In view of this, the present inventors made various trials in, for example, a so-called direct coating method in which a coating solution is pushed out from a nozzle onto the strut S. In a trial, dot coating was adopted in which the coating solution was applied in the form of dots. In another trial, the material thickness of the drug coat layer 10 formed on the outer surface of the strut S was varied partially. In a further trial, coating along the strut S is not conducted over the whole width of the strut S, and the shape of application route of the drug coat layer 10 on the outer surface of the strut S was selected. As a result, the inventors discovered that even in the case of a drug coat layer 10 united with the strut S and is less liable to be extended or flexed and is brittle, the layer 10 can deform following the extending deformation or compressing deformation of the strut S and the layer 10 can be prevented from cracking, peeling, destruction, damaging or falling off.

From this point of view, in this embodiment, the material thickness of the drug coat layer 10 on the outer surface of the strut S is varied, and the shape of the application route is selected. Combining these approaches helps ensure that the drug coat layer 10 can be deformed in a manner generally following the deformation of the strut S.

As shown in FIGS. 4 and 5, the drug coat layer 10 in this embodiment is so formed that its shape in cross-section perpendicular to the axis of the strut S is mountain shape. And the ridgeline R, which is a line following the crest of the mountain shape (i.e., following the portion of greatest thickness), extends in a zigzag, meandering or wavy shape (hereinafter generically referred to simply as "wavy shape") along the longitudinal direction or extent of the strut S.

With this wavy configuration of the ridgeline R, the position of the portion of the coating of greatest thickness in the width-wise direction of the strut varies (e.g., varies continuously) along at least a portion of the longitudinal extent of the strut S, preferably along the entire longitudinal extent of the strut S. The ridgeline R is not parallel to the central axis of the strut S. The ridgeline R deviates from the longitudinal centerline of the strut, being located closer to one longitudinally extending side edge of the strut than the other longitudinally extending side edge at certain places along the length of the strut as shown in FIG. 2, and being located closer to the other longitudinally extending side edge of the strut than the one longitudinally extending side edge at other places along the length of the strut. The ridgeline R crosses the longitudinal centerline of the strut at a plurality of spaced apart locations as shown in FIGS. 4 and 5. More specifically, FIGS. 4 and 5 illustrate that the ridgeline R of the drug coat layer on each strut (curved part or bend) crosses the longitudinal centerline of the strut at a plurality of spaced apart locations so that for each curved part, the ridgeline is positioned entirely on one side of the longitudinal centerline over one longitudinal portion of the strut and is positioned entirely on the opposite side of the longitudinal centerline over a different longitudinal portion of the strut.

This disclosed embodiment thus adopts both the variation in the material thickness of the drug coat layer 10 and the wavy configuration of the ridgeline R, to help ensure that even when the various parts of the strut S (e.g., the bends K and the straight parts T) are deformed, the drug coat layer 10 is also able to deform in a manner generally following this deformation so that the drug coat layer 10 is inhibited or prevented from peeling or rupture.

Herein, the apex (crest) of the mountain shape will be referred to as "apex Z," while the peak (vertex) of the wavy ridgeline shape (the portion corresponding to the inflection point of the wavy shape of the ridgeline R as viewed in plan view) will be referred to as "peak P."

The area of the drug coat layer 10 which is located in the vicinity of the inner-side inflection point 11 in the bend K is preferably formed using a small amount of the coating material. In other words, this area is preferably relatively thin compared to other parts (considered with respect to the widthwise direction of the strut). In the vicinity of the inner-side inflection point 11, the strut S undergoes an extending (expanding) action. Therefore, when the material thickness of the drug coat layer 10 in this area is relatively small (thin), the drug coat layer 10 is able to more easily deform in a manner following the extending deformation of the strut S, and so cracking of the coating is less liable to occur.

The area of the drug coat layer 10 which is located in the vicinity of the outer-side inflection point 13 in the bend K preferably includes a large amount of the coating material. In other words, this area is preferably relatively thick compared to other parts (considered with respect to the width-wise direction of the strut). In the vicinity of the outer-side inflection point 13, the strut S undergoes or experiences compression. However, this area is an area where the deformation amount of the strut S itself is smaller and the drug coat layer 10 is less susceptible to peeling or collapse, as compared to the area in the vicinity of the inner-side inflection point 11. Therefore, even when the drug coat layer 10 is formed to be thick in this area, the layer 10 can follow the compression deformation to some extent, and, moreover, a predetermined quantity of the drug can be secured easily.

In the vicinity of the inner-side inflection point 11, there are parts (small deformation parts) 15, 16 where the strut S is less liable to be deformed and is little deformed. At the small deformation parts 15, 16, the peaks P of the wavy ridgeline shape are located so that the drug is present there in a relatively large quantity.

In FIG. 5, the straight line connecting the center of curvature O (the center of curvature of both the inner-side of the bend and the outer-side of the bend) to the small deformation part 15, 16 is represented by the lines A-A, C-C respectively. The point at which the line A-A, C-C connecting the center of curvature O with the small deformation part 15, 16 respectively intersects the outer-side borderline 17 is indicated by the intersection 18, 19 respectively. The profile of a drug section interconnecting the small deformation part 15, 16 with the intersection 18, 19 is such that the amount of the drug increases steeply from the small deformation part 15, 16 to the apex Z of the mountain shape and decreases gradually from the apex Z to the intersection 18, 19.

In FIG. 5, the line connecting the center of curvature O to the inner-side inflection point 11 and the outer-side inflection point 13 is line B-B.

In practice, the bend K is rarely in the shape of a perfect circular arc. As shown in FIG. 5, the bend K may transit to a straight part T via a circular-arched part E, or may transit to a reverse circular-arched part Ea via the circular-arched part E. A boundary portion between the bend K and the straight part T or a boundary portion between the bend K and the reverse circular-arched part Ea is a portion which undergoes an extending (expanding) action corresponding to the inner-side inflection point 11 or the outer-side inflection point 13. Therefore, the amount of the drug at the boundary portion is the same as that at the inflection point 11, 13; in other words, the inner-side boundary portion and the outer-side boundary portion are set to be thin and thick, respectively.

Figure 6:
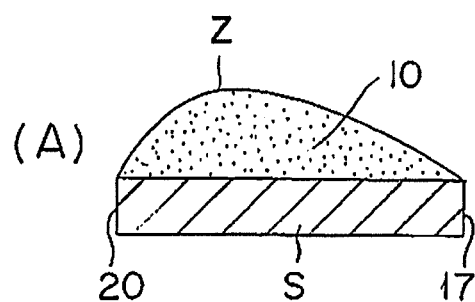
Figure 6:
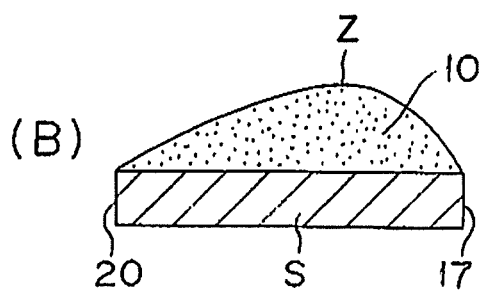
Figure 6:
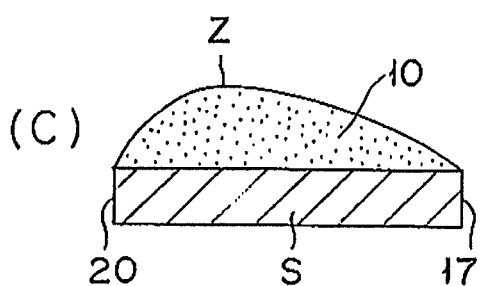
Figure 6:
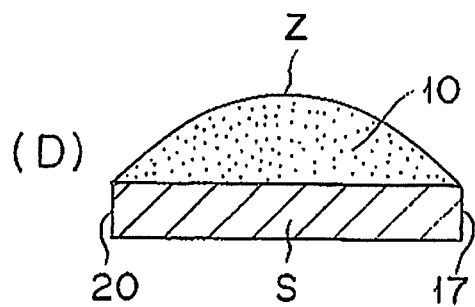
Figure 7:
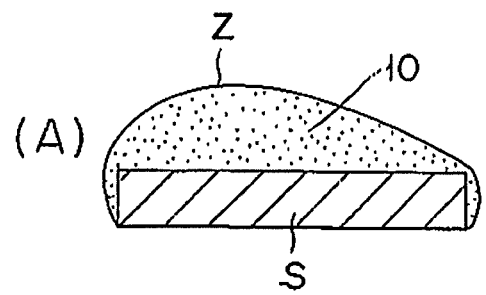
Figure 7:
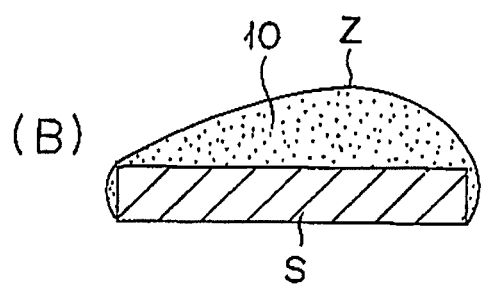
Figure 7:
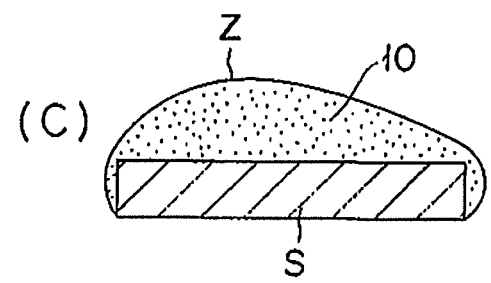
Figure 7:
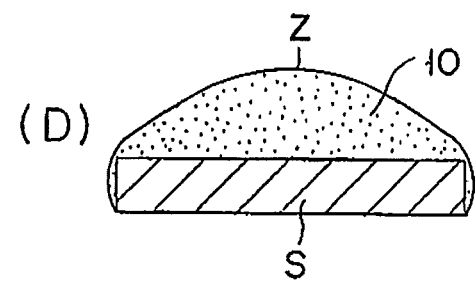

The cross-sectional configuration of the regions of the strut as discussed above are as shown in FIGS. 6 and 7. The cross-sectional shape of the drug coat layer 10 corresponding to line B-B in FIGS. 4 and 5 which passes through the inner-side inflection point 11 and the outer-side inflection point 13 is a mountain shape in which the apex Z (thickest portion or thickest region) is displaced from the center toward the side of the outer-side borderline 17 as shown in FIG. 6(B).

The cross-sectional shape of the drug coat layer 10 corresponding to line A-A or line C-C in FIGS. 4 and 5 which passes through the small deformation part 15 or 16 and the borderline intersection 18 or 19 is a mountain shape in which the apex Z is displaced from the center toward the side of the inner-side borderline 20, as shown in FIG. 6(A) or (C).

Incidentally, the sectional shape of the drug coat layer 10 corresponding to line D-D, located between line B-B and line C-C in FIG. 4, is a mountain shape in which the apex Z is located at the center, as shown in FIG. 6(D).

The cross-sectional shape of the drug coat layer 10 may not necessarily be formed so as to terminate at the inner-side borderline 20 or the outer-side borderline 17 of the strut S as shown in FIGS. 6(A)-6(D). For example, the cross-sectional shape may be so formed as to cover the inner-side borderline (inner side edge) 20 and the outer-side borderline (outer side edge) 17 as well as shown in FIGS. 7(A)-7(D). One benefit to this alternative configuration is that the amount of drug can be increased.

Figure 8:
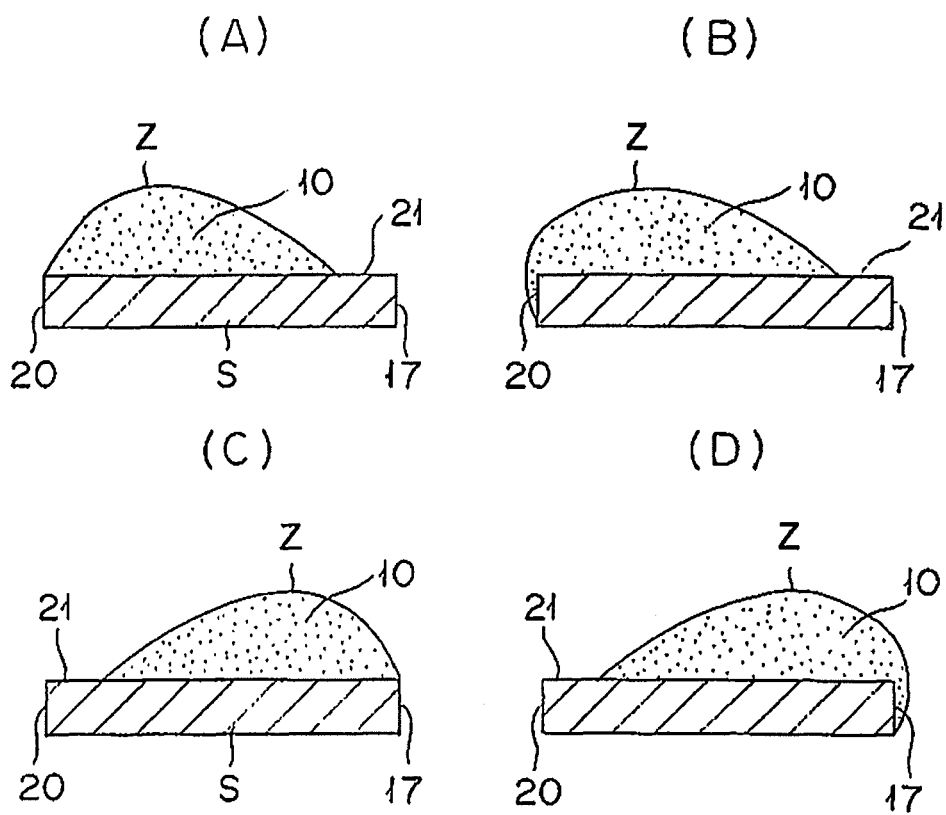

In addition, as represented by the drug coat layer 10 shown in FIG. 8, the cross-sectional shape of the drug coat layer 10 may be formed so that it terminates before reaching the inner-side borderline 20 or the outer-side borderline 17 of the strut S. In this case, the portion of the bend K in the vicinity of the inner-side borderline 20 or the outer-side border line 17 is a non-coated region 21 of the strut S that is devoid of the drug coat layer 10. This configuration helps ensure that the drug coat layer 10 is absent in the areas where strain is maximized, so that the peeling-restraining effect is further enhanced.

In the configuration in which the material thickness of the drug coat layer 10 is varied as discussed above, the drug coat layer 10 is formed so that its shape in a transverse cross-section perpendicular to the axis of the strut S is mountain shape. In addition, to permit the drug coat layer 10 to follow deformation of the strut S, the ridgeline R of the mountain shape extends in a wavy shape along the longitudinal direction or extent of the strut S. The ridgeline R possessing this wavy shape helps to ensure that even when the strut S is deformed, the drug coat layer 10 itself is also easily deformed, with the peak P of the wavy shape as the center of deformation. Consequently, the drug coat layer 10 is deformed in a manner following the deformation of the strut S so that the drug coat layer 10 can be inhibited or prevented from cracking, peeling or collapsing.

The pitch of the wavy ridgeline R or the number of peaks P can be varied in a manner desired so long as the drug coat layer 10 is able to follow the deformation of the strut S. It is to be noted, at least, that the drug coat layer 10 is preferably so formed that the number of peaks P present in the bend K is an odd number as shown in FIG. 5.

In FIG. 5, the terminal portions of the bend K are indicated by line X1-X1 and line X2-X2. When an odd number of peaks P are provided between the terminal portions at regular intervals, the inflection points 11 or 13 constituting turning points at which the drug coat layer 10 is deformed in the bend K is dispersedly arranged in a pattern of being staggered to the inner side and the outer side. Therefore, when the bend K is deformed, dispersion of strain is secured on a material thickness basis and on a shape basis, whereby the peeling-restraining effect is enhanced. Moreover, since the peak P of the drug coat layer 10 is present in the vicinity of the outer-side inflection point 13, the drug coat layer 10 can be deformed with the outer-side inflection point 13 as a center of deformation. Consequently, deformation of the drug coat layer 10 is balanced, with the outer-side inflection point 13 as a center, whereby the peeling-restraining effect is further enhanced.

The variation in material thickness of the drug coat layer 10 and the wavy shape of the drug coat layer 10 may be made in the bend K or in the straight part T, and may be made for the whole of the stent body 2 or in a part of the stent body 2. This helps ensure that the drug coat layer 10 can be physically deformed in a manner following the deformation of the stent body 2, without using plasticizer, so that the drug coat layer 10 can be inhibited or prevented from peeling or destruction.

For example, as shown in FIG. 5, the drug coat layer 10 may be configured so that the drug coat layer 10 is wavy in the bends K. In other portions, the drug coat layer 10 can be formed so that the ridgeline R of the mountain shape layer 10 meanders or, in some cases, is straight so as to substantially pass through the longitudinal center of the strut S as indicated by broken lines in FIG. 5. The wavy drug coat layer 10 may be formed not only in the bends K but also in the whole or a part of the outer surface of the strut S along the longitudinal direction or extent of the strut. This helps ensure that even where the stent body 2 is deformed locally, the strain exerted on the drug coat layer can be dispersed, whereby the peeling-restraining effect is further enhanced.

A variety of methods can be employed to apply to the outer surface of the strut(s) S the drug coat layer 10 having the varying material thickness and/or wavy shape described above. It is preferable, however, to use a lamination method in which a process of direct coating with a coating solution along the struts S is repeated a large number of times. In the lamination method, first the coating solution is ejected from a nozzle onto the outer surface of the struts S, whereby a predetermined area of the outer surface of the struts S is coated. Then, the coating solution thus applied is dried and solidified to form a thin drug coat layer 10 as a lowermost, first layer. Thereafter, the coating solution is again ejected from the nozzle onto a predetermined position on the thin drug coat layer 10 formed as the first layer to form a thin drug coat layer 10 as a second layer. The operation of thus forming the thin drug coat layer 10 in a laminating manner is repeated, whereby a drug coat layer 10 that is mountain-shaped in transverse cross section perpendicular to the axis of the struts S is formed on the outer surface of the struts S. The material thickness of each one of the thin drug coat layers 10 is 1 to 2 µm, and ten to thirty such thin drug coat layers 10 are laminated or applied to form a drug coat layer 10 having a material thickness of 10 to 30 µm.

The bore diameter of the nozzle to be used here is preferably about several tens of micrometers when the width of the struts S is 90 to 100 µm. It is to be noted, however, that the nozzle should have a predetermined bore diameter according to the viscosity and/or density of the coating solution.

While the drug coat layer 10 is composed of a mixture of a drug and a polymer, the mixture is preferably composed of a mixture of a drug and a biodegradable polymer. After the stent is indwelled in a living body, the polymer covering and protecting the drug is biodegraded so that the drug is released in a sustained manner, whereby restenosis in the stent indwelling lesion is prevented from occurring. As the biodegradable polymer, there is preferably used any of polylactic acid, polyglycolic acid, and a lactic acid-glycolic acid copolymer.

FIG. 9 is a front view of a living organ dilating device. The stent 1 is positioned in a blood vessel and left indwelling by use of, for example, a living organ dilating device as shown in FIG. 9. The living organ dilating device 30 includes: a shaft body 33 having a double tube structure composed of an inner tube 31 and an outer tube 32 which are disposed concentrically; a balloon 34 at a distal end of the shaft body 33 and capable of being folded and dilated; and a branch hub 36 having an injection port 35 for injecting a balloon-dilating fluid. The stent 1 is so mounted as to envelope the balloon 34 in a folded state.

The distal end of the inner tube 31 is opened, and the inner tube 31 includes a guide wire lumen in which a guide wire is inserted. The gap between the inner tube 31 and the outer tube 32 constitutes a lumen through which the balloon-dilating fluid passes. The balloon-dilating fluid is injected via the injection port 35, and enters the balloon 34, to dilate (radially outwardly expand) the balloon 34.

It is preferable that a radiopaque member is fixed to the outer surface of the inner tube 31 at a position corresponding to a central portion of the stent 1 so that the position of the stent 1 can be visually confirmed during radioscopy.

Now, the use and operation of the device will be described below.

First, the living organ dilating device 30 and the stent 1 provided with the drug coat layer 10 on the outer surface of the struts S are prepared. The balloon 34 provided at a distal end of the living organ dilating device 30 is in a folded state, the stent 1 is mounted on the folded balloon, and the stent 1 is radially contracted so that the stent is in a radially contracted state. In this condition, the distal end of the living organ dilating device 30 is inserted into a living body, and is brought to a predetermined lesion in the living body while visually confirming the position of the stent 1 by the image of the radiopaque member. In this embodiment, the drug coat layer 10 provided on the outer surface of the struts S is in the state of being firmly bonded to the struts S, so that the drug coat layer 10 is free of the risk of peeling due to friction with the living body, even during delivery of the stent 1.

When the stent 1 is visually confirmed to have reached the predetermined lesion in the living body, a balloon-dilating fluid is injected via the injection port 35 to dilate the balloon 34.

Dilating or expanding the balloon 34 causes the stent 1 to also be expanded in the radial direction. The expansion of the stent 1 is achieved by a process in which the portions of the U-shaped struts S constituting the bends K are mutually opened wider so that the bends K are spaced farther away from the horizontal parts H1, as shown in FIG. 3.

Specifically, as shown in FIG. 5, when the mutual spacing between the portions of the U-shaped strut S is opened wider, an extending (expanding) action is applied to the inner-side inflection point 11, while a compressing action is applied to the outer-side inflection point 13. In this case, since the drug coat layer 10 provided on the outer surface of the strut S is thin at the inner-side inflection point 11, the drug coat layer follows the extending deformation of the strut S so that cracking would not occur there. On the other hand, though the drug coat layer 10 is thick at the outer-side inflection point 13, the deformation amount of the strut S itself at the outer-side inflection point 13 is small and so the drug coat layer 10 follows the compressing deformation of the strut S and therefore is not so susceptible to peeling or collapse there. Moreover, since the drug coat layer 10 is mountain-shaped in cross-section and the ridgeline R of the mountain shape extends in a wavy shape along the longitudinal direction or longitudinal extent of the strut S, the drug coat layer 10 is easily deformed and is able to follow the deformation of the strut S. Therefore, the drug coat layer 10 follows the deformation of the strut S on a shape basis, so that the risk of cracking, peeling or collapse of the drug coat layer 10 is remarkably lowered. Accordingly, the drug coat layer 10 can retain its initial state even when the stent 1 is expanded by the balloon 34.

Consequently, even upon expansion of the stent 1 by the balloon 34, an amount of the drug in the drug coat layer 10 is secured, the drug is slowly eluted from the stent 1 left indwelling in the living body, to exhibit its medicinal efficacy and prevent restenosis.

The stent disclosed here is not limited to the above-described embodiment, as modifications can be made by those skilled in the art in general keeping with the disclosure here. For instance, while the stent is a stent having the pattern or configuration in the above-described embodiment, the stent is not limited only to the thus-described stent, and may be a differently constructed stent 1 such as shown in FIG. 10. The stent 1 in FIG. 10 has a configuration in which bends K of struts S are mutually joined while intersecting at joints F, and the joints F are interconnected through each of straight parts T. The straight parts, the parallel parts, and the wavy parts are examples of longitudinally extending parts of the stent body, various ones of which are connected together by the curved parts or bends, which can be U-shaped in form.

The present invention can be utilized as a stent for markedly reducing the restenosis rate of a dilated lesion after percutaneous transluminal coronary angioplasty (PTCA).

The detailed description above describes features and aspects of the stent disclosed here. But the invention is not limited to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent comprising: a longitudinally extending stent body that includes a plurality of axially arranged annular members in which axially adjacent annular members are connected to one another, each annular member comprising a plurality of longitudinally extending parts each possessing a width-wise extent and a lengthwise-extent, the plurality of longitudinally extending parts being connected to one another by curved parts each possessing a width-wise extent and a lengthwise-extent;

the stent body being radially outwardly expandable from a contracted state to an expanded state, the curved parts being deformed during the radial outward expansion of the stent body;

a drug coat layer on an outer surface of a plurality of the curved parts of each of the plurality of annular members;

the drug coat layer on each of the plurality of curved parts varying in thickness in the width-wise extent of the respective curved part, the drug coat layer on each of the plurality of curved parts possessing a ridgeline extending along a lengthwise extent of the respective curved part, the ridgeline being the portion of the drug coat layer having the greatest thickness;

the ridgeline of the drug coat layer on each curved part crossing a longitudinal centerline of the curved part at a plurality of spaced apart locations so that for each curved part, the ridgeline is positioned entirely on one side of the longitudinal centerline over one longitudinal portion of the curved part and is positioned entirely on the opposite side of the longitudinal centerline over a different longitudinal portion of the curved part; and the drug coat layer possessing a longitudinal centerline, wherein at least a portion of the ridgeline of the drug coat layer crosses the longitudinal centerline of the drug coat layer at a plurality of spaced apart locations.

2. The stent according to claim 1, wherein: each curved part includes an inner curved surface and an outer curved surface positioned radially outwardly of the inner curved surface; the outer curved surface possesses a larger radius of curvature than the inner curved surface, the inner curved surface has an inner-side inflection point and the outer curved surface has an outer-side inflection point, with a reference line passing through a center of curvature of the inner curved surface, through the inner-side inflection point, and through the outer-side inflection point; the ridgeline at the reference line is located closer to the outer-side inflection point than the inner-side inflection point.

3. The stent according to claim 1, wherein: each curved part includes an inner curved surface and an outer curved surface positioned radially outwardly of the inner curved surface; the outer curved surface possesses a larger radius of curvature than the inner curved surface, the inner curved surface has an inner-side inflection point and the outer curved surface has an outer-side inflection point, with a reference line passing through a center of curvature of the inner curved surface, through the inner-side inflection point, and through the outer-side inflection point; a portion of the curved part at the reference line being devoid of the drug coat layer closer to the inner-side inflection point.

4. The stent according to claim 1, wherein the ridgeline is wavy and includes a plurality of peaks, the plurality of peaks in each curved part being an odd number of peaks.

5. The stent according to claim 1, wherein in each of the curve parts the drug coat layer is also provided on an inner side edge and on an outer side edge of the curve part.

6. The stent according to claim 1, wherein the drug coat layer comprises a mixture of a drug and a polymer.

7. The stent according to claim 6, wherein the polymer is a biodegradable polymer.

8. A stent comprising:

a longitudinally extending stent body in which a plurality of annular members are arranged axially, with axially adjacent annular members connected to one another;

each annular member including a plurality of interconnected struts each having a longitudinal centerline along a longitudinal extent of the strut, each strut also having a width-wise extent and a lengthwise-extent, the struts including curved parts and longitudinally extending parts;

the stent body being radially outwardly expandable from a contracted state to an expanded state, and causing at least some of the struts to deform;

a drug coat layer on an outer surface of a plurality of the struts of each of the plurality of annular members;

the drug coat layer on each strut varying in thickness in the width-wise extent of the respective strut, a width-wise location of the greatest thickness of the drug coat layer on each strut varying along the lengthwise extent of the strut;

the drug coat layer having a ridgeline which follows the portion of the drug coat layer having the greatest thickness; and the drug coat layer possessing a longitudinal centerline, wherein at least a portion of the ridgeline of the drug coat layer is wavy-shaped with respect to the longitudinal centerline such that it crosses the longitudinal centerline of the drug coat layer at a plurality of spaced apart locations.

9. The stent according to claim 8, wherein: the drug coat layer is on one of the curved parts, the curved part including an inner curved surface and an outer curved surface, the outer curved surface being positioned radially outwardly of the inner curved surface; the outer curved surface possesses a larger radius of curvature than the inner curved surface; the inner curved surface has an inner-side inflection point and the outer curved surface has an outer-side inflection point, with a reference line passing through a center of curvature of the inner curved surface, through the inner-side inflection point, and through the outer-side inflection point; the ridgeline at the reference line is located closer to the outer-side inflection point than the inner-side inflection point.

10. The stent according to claim 8, wherein: the drug coat layer is on one of the curved parts, the curved part including an inner curved surface and an outer curved surface, the outer curved surface being positioned radially outwardly of the inner curved surface; the outer curved surface possesses a larger radius of curvature than the inner curved surface; the inner curved surface has an inner-side inflection point and the outer curved surface has an outer-side inflection point, with a reference line passing through a center of curvature of the inner curved surface, through the inner-side inflection point, and through the outer-side inflection point; a portion of the curved part at the reference line being devoid of the drug coat layer, the portion of the curved part devoid of the drug coat layer being closer to the inner-side inflection point than the outer-side inflection point.

11. The stent according to claim 8, wherein the wavy-shaped ridgeline includes a plurality of peaks, the plurality of peaks in each curved part being an odd number of peaks.

12. A stent comprising: a tubular stent body having struts intersecting at joints, the stent body being expandable and contractible in a radial direction, the struts each having an axis;

a drug coat layer coating outer surfaces of the struts;

at least one of the struts having a bend which is deformed as the stent body expands or contracts in the radial direction, and the drug coat layer on the outer surface of the bend having a convex shape in a cross-section perpendicular to the axis of the at least one strut, a ridgeline of the drug coat layer extending in a wavy shape along a longitudinal extent of the at least one strut; and the drug coat layer possessing a longitudinal centerline, wherein at least a portion of the ridgeline of the drug coat layer is wavy-shaped with respect to the longitudinal centerline of the drug coat layer such that it crosses the longitudinal centerline of the drug coat layer at a plurality of spaced apart locations.

13. The stent according to claim 12, wherein the bend is bent in a gradual circular arched shape.

14. The stent according to claim 12, wherein the bend is deformed to be opened wider when the stent body is expanded radially outward, and the drug coat layer is on the outer surface of the bend in such a manner that a peak of the wavy-shaped ridgeline is located farther from an inner-side inflection point of the bend and closer to an outer-side inflection point of the bend where a compressive action due to the opening-wider deformation is applied.

15. The stent according to claim 12, wherein the bend is deformed to be opened wider when the stent body is expanded radially outward, the bend on which the drug coat layer exists including a non-coated portion devoid of the drug coat layer, the non-coated portion being farther from an outer-side inflection point of the bend and closer to an inner-side inflection point of the bend where an expansive compressive action due to the opening-wider deformation is applied.

16. The stent according to claim 12, wherein the bend is provided with the drug coat layer in such a manner that an odd number of peaks of the wavy-shaped ridgeline are present.

17. The stent according to claim 12, wherein the drug coat layer is formed on a whole or a part of the outer surface of the at least one strut in such a manner that the ridgeline of the drug coat layer extends in a wavy shape along the longitudinal direction of the at least one strut.

18. The stent according to claim 12, wherein the drug coat layer comprises a mixture of a drug and a polymer.

19. The stent according to claim 18, wherein the polymer is a biodegradable polymer.

20. The stent according to claim 19, wherein the biodegradable polymer is any of polylactic acid, polyglycolic acid, and a lactic acid-glycolic acid copolymer.

* * * * *